United States Patent [19]
Parrott et al.

[11] Patent Number: 6,096,523
[45] Date of Patent: Aug. 1, 2000

[54] TRANSFORMATION VECTOR SYSTEM

[75] Inventors: Wayne A. Parrott, Athens, Ga.; J. Michael Thomson, Gainesville, Fla.

[73] Assignee: University of Georgia Research Foundation, Athens, Ga.

[21] Appl. No.: 09/185,886

[22] Filed: Nov. 4, 1998

[51] Int. Cl.⁷ .................................................. C12N 15/66
[52] U.S. Cl. .................... 435/91.41; 435/196; 435/320.1
[58] Field of Search ............................. 435/320.1, 91.41, 435/196, 440

[56] References Cited

U.S. PATENT DOCUMENTS

| | | | |
|---|---|---|---|
| 4,766,072 | 8/1988 | Jendrisak et al. ...................... | 435/91.1 |
| 5,017,488 | 5/1991 | McAllister ............................... | 435/194 |
| 5,037,745 | 8/1991 | McAllister ............................... | 435/91.1 |
| 5,420,032 | 5/1995 | Marshall et al. . | |
| 5,474,896 | 12/1995 | Dujon et al. . | |

OTHER PUBLICATIONS

Lonsdale, D.M. et al. "pFC1 to pFC7: A Novel Family of Combinatorial Cloning Vectors"; (1995) *Plant Molecular Biology Reporter* 13(4):343–345.

Asselbergs, F.A.M. et al. "Creation of a Novel, Versatile Multiple Cloning Site Cut by Four Rare–Cutting Homing Endonucleases"; (1996) *BioTechniques* 20:558–562.

Bloch, C.A. et al. "Purification of *Escherichia coli* Chromosomal Segments without Cloning"; (1996) *Biochem. Biophys. Res. Comm.* 223:104–111.

Muscarella, D.E. et al. "Characterization of I–Ppo, an Intron–Encoded Endonuclease That Mediates Homing of a Group I Intron in the Ribosmoal DNA of *Physarum polycephalum*"; (1990) *Mol. Cell. Biol.* 19:3386–3396.

Perler, F.B. et al. "Intervening sequences in an Archaea DNA polymerase gene"; (1992) *Proc. Natl. Acad. Sci. USA* 89:5577–5581.

Xu, M.Q. et al. "In Vitro Protein Splicing of Purified Precursor and the Identification of a Branched Intermediate"; (1993) *Cell* 75:1371–1377.

*Primary Examiner*—James Ketter
*Attorney, Agent, or Firm*—Greenlee Winner and Sullivan PC

[57] ABSTRACT

The present invention provides a vector system that includes a set of shuttle vectors and a docking vector such that individual DNA segments, including large segments of coding DNA, can be cloned into individual shuttle vectors in the desired orientation and combined in a desired order and orientation, into a single docking vector. The docking vector can serve as a transformation vehicle directly or as a starting point from which the entire combination can be transferred to other transformation means.

20 Claims, 3 Drawing Sheets

SEQUENCE LISTING

<160> NUMBER OF SEQ ID NOS: 6

<210> SEQ ID NO 1
<211> LENGTH: 251
<212> TYPE: DNA
<213> ORGANISM: Artificial Sequence
<220> FEATURE:
<223> OTHER INFORMATION: Description of Artificial Sequence: linker for
      use in cloning

<400> SEQUENCE: 1
agtgaattca cattaacccct cactaaaggg agatatcgat cactagtgcg gccgcaccgg      60
taccatggat cctcgaggcg cgccagatct agacgtacgt ggccaattgg gcccttaatt     120
aaggcctcgt ttaaacagtc gacgtcgccc gggctgcagc atgcatttaa atggctagcg     180
gccggcctag ggaccgcggt taacatctcc ctatagtgag tcgtattaaa gcttggcgta     240
atcatggtca t                                                         251

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: linker

<400> SEQUENCE: 2
taactataac ggtcctaagg tagcga                                          26

<210> SEQ ID NO 3

-continued

```
<211> LENGTH: 23
<212> TYPE: DNA
<213> ORGANISM: Artificial Sequence
<220> FEATURE:
<223> OTHER INFORMATION: Description of Artificial Sequence: linker

<400> SEQUENCE: 3
atgactctct taaggtagcc aaa                                              23

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: linker

<400> SEQUENCE: 4
tggcaaacag ctattatggg tattatgggt                                       30

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: linker

<400> SEQUENCE: 5
atctatgtcg ggtgcggaga aagaggtaat gaaatggca                             39

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: linker

<400> SEQUENCE: 6
ggttctttat gcggacactg acggctttat g                                     31
```

TRANSFORMATION VECTOR SYSTEM

ACKNOWLEDGMENT OF FEDERAL RESEARCH SUPPORT

The invention has been made in part with grant assistance from the U.S. Government under the Hatch Act, Grant No. GEO-00712. The U.S. Government therefore has certain rights in the invention.

BACKGROUND OF THE INVENTION

The isolation, cloning, transfer and recombination of DNA segments, including coding sequences and non-coding sequences, is most conveniently carried out using restriction endonuclease enzymes. Restriction endonucleases are especially useful because each one introduces a hydrolytic cleavage of a phophodiester bond linking adjacent nucleotides of a DNA structure only at a specific, defined site. The site of cleavage is defined by a sequence of nucleotides surrounding or adjacent to the cleavage site. Over one hundred such enzymes are now known, and the sites at which they act, termed restriction sites, are defined. For the majority of such enzymes, the nucleotide sequence defining the restriction site and the bonds cleaved is specific for each enzyme. In some cases, different enzymes recognize the same site or a variant, such as the same sequence with a methylated base, or a shorter subsequence, and act to hydrolyze the same bond, or different bonds within or adjacent to the recognition sequence. Some restriction enzymes hydrolyze bonds adjacent to complementary bases on double-stranded DNA, producing "blunt ends." Others produce staggered cuts which result in the DNA having overlapping complementary or "sticky" ends.

The distribution of restriction sites throughout the genome of an organism is essentially random; except for areas where sequence repeats occur. The frequency of occurrence of a given restriction site is therefore primarily a function of the combinatorial likelihood of the proper nucleotides occurring in the proper sequence. Therefore, restriction sites having shorter nucleotide sequences occur with greater frequency than those with longer sequences. Consequently, if DNA is incubated with a restriction endonuclease that recognizes a four base restriction site sequence (a "four base cutter"), the resulting DNA fragments are, on average, shorter in length than those produced by the action of an endonuclease recognizing a six-base restriction site sequence (a "six-base cutter"). Given a 50% average GC content, the frequency of appearance of a given restriction site is $4^n$ where n is the number of bases that constitute the recognition site sequence (or more accurately, base pairs [bp] since the sites occur on double-stranded DNA). A site whose length is 4 bp will therefore occur with an average frequency of once every $4^4$=256 bp of DNA, which is the average length of DNA incubated with a 4-base cutter restriction endonuclease. Six-base cutters yield fragments whose calculated average length is $4^6$=4096 bp. Since the distribution of restriction sites is essentially random, many DNA fragments much larger or smaller than 4096 bp are found when DNA is cut with a given 6-base cutter endonuclease. By having a variety of six-base cutting endonucleases available, it is often possible to clone and transfer individual DNA segments much longer than 4096 bp. The need to clone and transfer larger DNA segments has been one factor driving the search for a greater variety restriction endonucleases.

In addition, the search has also yielded restriction enzymes with longer restriction site sequences. Of particular relevance herein are a set of endonucleases designated "rare-cutting" endonucleases, defined herein as those having a recognition site of 9 or more base pairs. The currently known rare-cutting endonucleases are encoded within introns, and their biological function appears to differ from the restriction endonucleases, which are also termed Type II endonucleases. The rare-cutting endonucleases are sometimes termed "homing-endonucleases" in the literature. For general reviews, see Lambowitz, A. M. et al (1993) *Ann. Rev. Biochem.* 62:587–622; Mueller, J. E. et al. (1993) "Homing endonucleases" in Nucleases (S. M. Linn, S. R. Lloyd and R. J. Roberts, Eds.) Cold Spring Harbor Press, Cold Spring Harbor, N.Y.; and Perler, F. B. et al (1994) *Nucl. Acids. Res.* 22:125–1127.

U.S. Pat. No. 5,420,032 (Marshall et al.) discloses homing endonuclease I-CeuI, together with its recognition site, which is 19 bp in length. The recognition sequence is somewhat degenerate, so that the actual cutting frequency is somewhat less than the theoretical $4^{19}$=2.7487×$10^{11}$ bp; nevertheless the existence of I-CeuI sites is very rare.

U.S. Pat. No. 5,474,896 (Dujon et al) discloses the endonuclease PI-SceI, together with DNA encoding the enzyme and characterization of the recognition sequence. The recognition sequence is 11 bp in length, making its calculated cutting frequency 1 in $4^{11}$=4,194,300 bp.

Other rare-cutting endonucleases have been described, including I-PpoI (Muscarella, D. E. et al [1990] *Mol. Cell. Biol.* 19:3386–3396); I-TliI (Perler, F. B. et al. [1992] *Proc. Natl. Acad. Sci. USA.* 89:5577–5581); and I-PspI (Xu, M. Q. et al. [1993] *Cell* 75:1371–1377). All the foregoing have 10 bp recognition sites, with a calculated cutting frequency of 1 in $4^{10}$=1,048,580. All of the above-described rare-cutting endonucleases are currently available from commercial sources, including New England Biolabs, Beverly, Mass. and/or Promega Corp., Madison, Wis.

The described rare-cutting endonucleases generate staggered cuts in double-stranded DNA, resulting in cut ends which have 4-base overlapping, self-complementary single stranded ends. A DNA segment cut with one of these nucleases can only be rejoined, using DNA ligase, to DNA cut in the same orientation, i.e., having the same complementary ends, except for I-PpoI where the single stranded ends generated by the enzyme have the same sequence regardless of the orientation of the restriction site sequence. Consequently these endonucleases (except I-PpoI) have the property of controlling the orientation of insertion of DNA cut with a given enzyme at a site on a vector cut with the same enzyme (or one generating the same complementary ends). In this regard, the property of generating self-complementary ends allowing for oriented vector insertion is shared by many conventional (Type II) restriction endonucleases and is commonly exploited by those skilled in the art to control the orientation of a DNA segment inserted into a vector, with respect to other genes or markers on the vector. Further, it is well-known that such oriented insertion can be by-passed, if desired, by known methods of removing the complementary ends ("blunt-ending") to allow rejoining by "blunt-end" ligation.

I-PpoI can be used to allow any DNA segment to be inserted into a vector in either orientation, with respect to markers on the vector. The enzymes I-PspI, I-TliI, PI-SceI and I-CeuI can be used to insert a DNA segment in a controlled orientation into a vector, depending on the orientation of the recognition sequence with respect to markers on the vector.

The rare-cutting endonucleases have been recognized as useful for excising and inserting large segments of DNA, for example in large-scale mapping, purifying native continuous/non-overlapping DNA segments and the like (Block, C. A. et al. (1996) *Biochem. Biophys. Res. Comm.* 223:104–111. In addition the rare-cutting endonuclease recognition sites have been incorporated into vectors for cloning and transferring DNA segments. Asselbergs, F. A. M. et al. (1996) *BioTechniques* 20:558–562 described vectors termed pI-LINK having a single copy of each of PI-SceI, I-PpoI, I-CeuI and I-TliI interspersed with fourteen conventional restriction sites in a single multiple cloning site. Variants having the same multiple cloning site flanking a neomycin resistance gene were also described.

SUMMARY OF THE INVENTION

Despite the availability of numerous conventional Type II restriction enzymes, including the discovery of a few 8-base cutters such as NotI and SfiI, it has remained a matter of great difficulty to combine two or more genes or other DNA segments of significant length together in a single vector for transformation. The problem is especially acute where it is desired to transform with two or more genes in tandem under control of a single regulatory element. The greater the number of segments to be combined for transformation and the larger the segment, the greater the problem. As more or larger segments are desired in combination, the number of useable restriction sites becomes vanishingly small because of the increasing likelihood that one such site will lie within one of the segments to be transferred. In addition, the prior manipulations required during cloning and during construction of shuttle vectors with the desired segment in desired orientation, and the manipulations designed to provide the appropriate recognition site sequences flanking the desired DNA segments quickly exhaust the number of available restriction enzymes that can be used to assemble the desired segments in the desired order and the desired orientation for transformation.

The present invention provides a vector system that includes a set of shuttle vectors and a docking vector such that individual DNA segments, including large segments of coding DNA, can be cloned into individual shuttle vectors in the desired orientation and combined in a desired order and orientation, into a single docking vector. The docking vector can serve as a transformation vehicle directly or as a starting point from which the entire combination can be transferred to other transformation means. The latter can include, without limitation, other types of transformation vectors such as binary vectors of Agrobacterium Ti plasmid, virus-based vectors, artificial chromosomes for bacteria or for yeast, incorporation into microprojectiles, needles, fibers and the like for facilitating cell penetration, or into liposomes, cationic lipid clusters, dendrimers and the like for facilitating DNA entry into cells, or as naked DNA.

Although previous studies have attempted to introduce two or more genes by co-transformation using individual vectors for each gene, it is difficult to synchronize the number of integration events attributable to the individual vectors. Co-transformation also makes it difficult to control the orientation of integration of the various different genes. As another stratagem, transgenic plants can be individually transformed, then crossed together. However, the presence of an independently segregating transgene greatly complicates the breeding of transgenic cultivars. The method is even less attractive when applied to animals, and is not feasible for gene therapy applications.

The vector system exemplified herein includes a multiple cloning site vector (designated pMECA, FIG. 1) which also includes a lac Z gene, ampicillin-resistance, and bacteriophage T3 and T7 promoters flanking the multiple cloning site in position to allow transcription in either direction. Insertions in pMECA can be detected either by a change in colony size or by blue/white screening based on lac Z gene activity. Other exemplified vectors in the system include a docking vector which includes within the multiple cloning site a plurality of rare-cutting endonuclease recognition sites positioned to allow sequential oriented insertion of DNA segments in a desired orientation, and a series of shuttle vectors which are designed to provide positional insertion and removal of individual DNA segments and to provide flanking DNA of the desired restriction site sequence for insertion into the docking vector.

Insertions in the docking and shuttle vectors can be detected based on PCR amplification using the bacteriophage T3 and T7 promoters flanking the multiple cloning sites, as well as standard endonuclease digestion and DNA sequencing.

DETAILED DESCRIPTION OF THE INVENTION

"Vector" denotes a DNA used as a carrier for a particular segment of DNA, capable of being transferred to a host organism. Typically, a vector is a plasmid, virus genome or artificial chromosome; however, as used herein, the term is not limited to these particular structures, but includes any DNA meeting the above definition. For convenience, the invention will be described hereinafter as applied to plasmid vectors. Vectors having more specialized functions are commonly referred to as transfer vector, expression vector, shuttle vector, binary vector, suicide vector, transformation vector and the like. Such terms are applied for convenience of description and are not necessarily limiting, since a given vector can serve several functions. Those skilled in the art can recognize the capabilities and limitations of a given vector, based on the genetic determinants carried on the vector.

"Shuttle" vector as used herein denotes a vector designed to serve as a carrier of a particular DNA segment from one vector to another. A shuttle vector is also used for combining particular DNA elements. For example, a shuttle vector of the invention is provided with a multiple cloning site with at least two rare-cutter restriction sites flanking at least one other restriction site. The two rare-cutter sites may be the same or different. By inserting a particular desired DNA segment into the vector at a middle site, then excising with the appropriate rare-cutting endonuclease, the desired DNA can be isolated with rare-cutter site sequence at either end. The desired DNA can then be readily inserted into any vector provided with the same rare cutting endonuclease site.

"Multiple cloning site" is a term well-known in the art, referring to a segment constructed to provide a plurality of restriction sites in essentially contiguous or overlapping array. A multiple cloning site provides versatility by allowing insertion at a defined locus on the vector using any one or combination of several restriction sites. If a sufficient number of different sites is provided, a series of integrations can be performed to introduce desired DNA segments in tandem into the vector. The invention provides a particularly versatile vector, pMECA, based on pUC 19 (Yannisch-Perron, C. et al [1985] *Gene* 33:103–119) and having a multiple cloning site with 44 unique restriction sites (Thomson, J. M. et al. [1998] *BioTechniques* 24:922–928 incorporated herein by reference). A multiple cloning site is sometimes termed a "polylinker" in the art.

"Rare cutter restriction site" is used herein to denote a restriction or homing endonuclease recognition site of at least 9 bp length. For a rare-cutting restriction site, the calculated average frequency of occurrence in DNA having a 50% average GC content is less than 1 in $4^9$=262,144 bp. In the published literature, recognition sites of 8 bp have been termed "rare"; however, such sites are excluded for purposes of the invention described herein.

Figure 3:
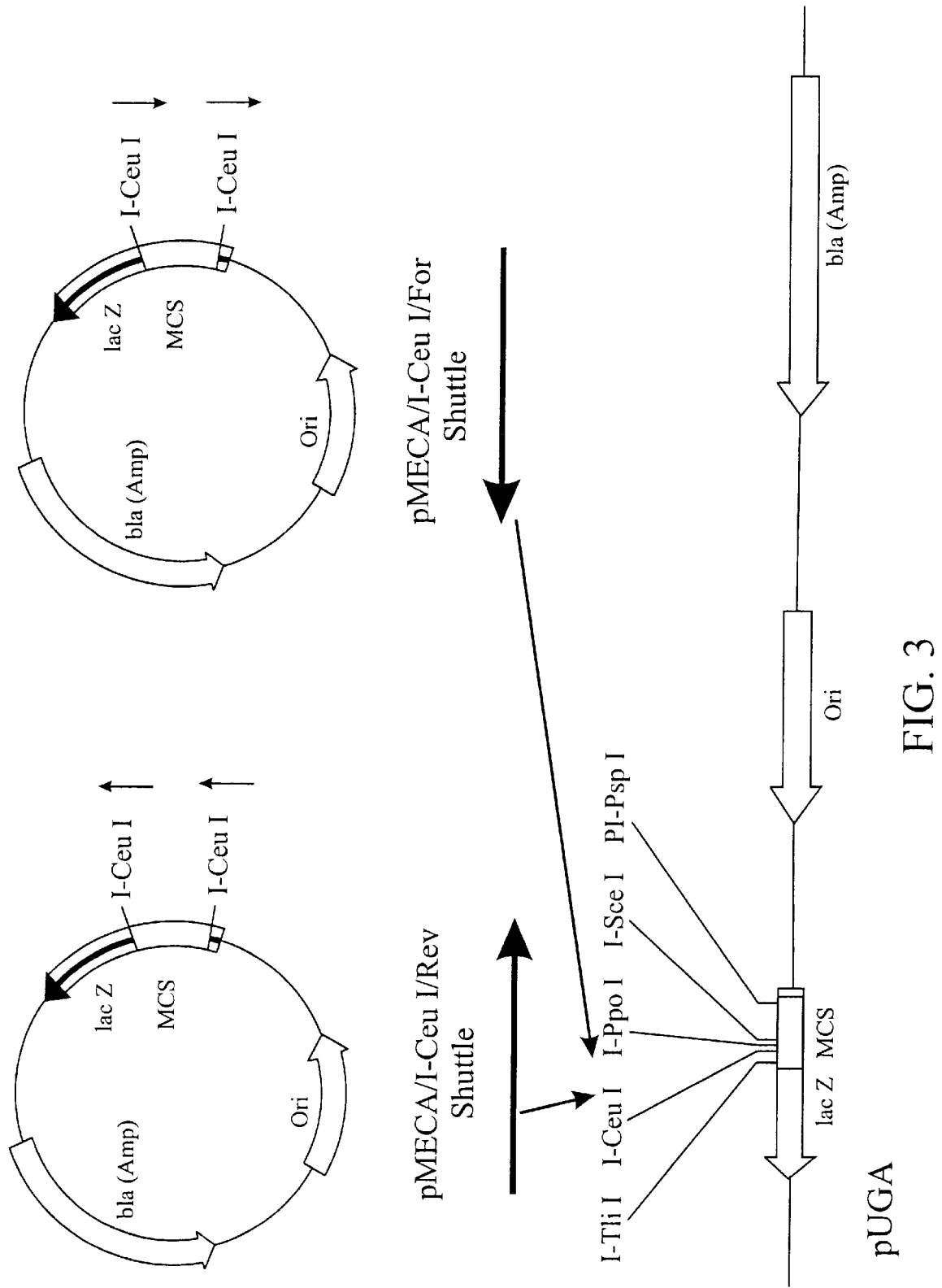
FIG. 3 is a diagram showing two shuttle vectors, identical except for orientation of the I-CeuI site orientations, together with a linear diagram of pUGA depicting transfer of a DNA segment from the shuttle to pUGA. Arrows beside each I-CeuI site indicate forward (down) or reverse (up) orientation of each site. Arrows under each vector diagram indicate an opposing orientation for DNA inserted in either "forward" or "reverse" orientation. The DNA insert orientation does not depict the direction of gene transcription, but is only shown to identify two possible orientations of the inserted DNA.

"Congruent orientation" is the term used to describe when two restriction sites are not in opposite polarity with one another. When the two sites are the same, their polarity on a vector is the same if, after cutting the vector with the enzyme specific to the sites and removing the intervening fragment, the cut ends can be annealed and re-ligated. Sites on a shuttle vector are congruent with a site or sites on a docking vector if a DNA segment lying between two sites on the shuttle can be inserted into the same site or sites on the docking vector in the same orientation as it was on the shuttle vector relative to other markers on the docking vector. FIG. 3 illustrates diagrammatically the transfer of a DNA segment cloned between two I-CeuI sites on a shuttle vector (either pMECA/I-CeuI-I-CeuI/For or pMECA/I-CeuI-I-CeuI/Rev can be transferred in either forward (congruent) or reverse (non-congruent) orientation to the docking vector pUGA, whose I-CeuI site is in forward orientation with respect to markers on the vector. When a DNA segment is cloned between two sites whose restriction enzymes generate asymmetric ends, each of these sites must be in the same orientation with respect to its counterpart on the docking vector, to permit insertion into the docking vector. The rare-cutting site I-PpoI has a symmetrical sticky end, such that the insertions into an I-PpoI site can occur in either polarity. Therefore, an I-PpoI site is in congruent orientation with any other site, regardless of the latter's orientation. By using shuttle vectors constructed with rare-cutting endonuclease sites of the proper polarity, desired DNA segments can be introduced into a docking vector, such as pUGA, in any desired combination of orientations.

As a matter of descriptive convention, since most vectors are circular, a given site or locus is said to be "between" two others if it is so located within the shortest intervening DNA segment on the plasmid. The opposite location (not between) is termed "flanking." For illustration, referring to FIG. 1, the multiple cloning site lies "between" the T7 promoter and the T3 promoter, and the two promoters are "flanking" the multiple cloning site.

A "docking vector" is the term used to denote a vector having a plurality of rare-cutting endonuclease sites within a multiple cloning site to allow separate insertions of particular DNA segments in defined orientation with respect to one another. A docking vector having the rare-cutting sites in congruent orientation with one another can be used for stacking a plurality of genes or open reading frames which, depending on their construction and control elements, can be coordinately expressed or individually expressed in a transformed host cell. The invention is exemplified by a docking vector, pUGA, having five rare-cutting sites in "forward" orientation, which allows for separately inserting up to nine DNA segments in a defined order and orientation with respect to one another.

The invention is further described by reference to a particular set of cloning, shuttle and docking vectors, described in detail. The basic vector can be any vector suitable for accepting and replicating DNA insertions of the desired size, having appropriate marker genes and selection genes, as is understood in the art. The rare-cutter restriction sites are described in "forward" orientation, as shown in the figures. It will be understood that the vectors can be designed for insertion of DNA desired. All the vectors described herein are variants of, or derived from the basic pMECA vector; however, there is no fundamental requirement that the shuttle vectors and docking vector be related or share common features, other than those minimally required for use in accordance with the invention.

A large number and variety of vectors is known in the art. Reference is made to Pouwels, P. H., et al (1985) *Cloning Vectors, a Laboratory Manual* (Elsevier, Amsterdam) as well as subsequent updates thereof. A total of over 1,000 vectors is described therein, including genetic maps and restriction maps thereof. One skilled in the art can readily select suitable vectors for use in *E. coli*, other gram negative bacteria, gram positive bacteria, Yeasts, Fungi, Streptomycetes, plant cells, animal cells as well as other cell types. Most widely used vectors are commercially available from sources such as New England Biological, Beverly, Mass., Life Technologies, Gaithersberg, Md., Stratagene, La Jolla, Calif., and ProMega, Madison, Wis. Factors affecting vector choice are known in the art: type of replicon, nature and location of selection markers, nature and location of restriction sites suitable for inserting a DNA segment characteristic of the invention for converting a known vector into a shuttle vector of the invention, or into a docking vector, as herein described.

Figure 1:
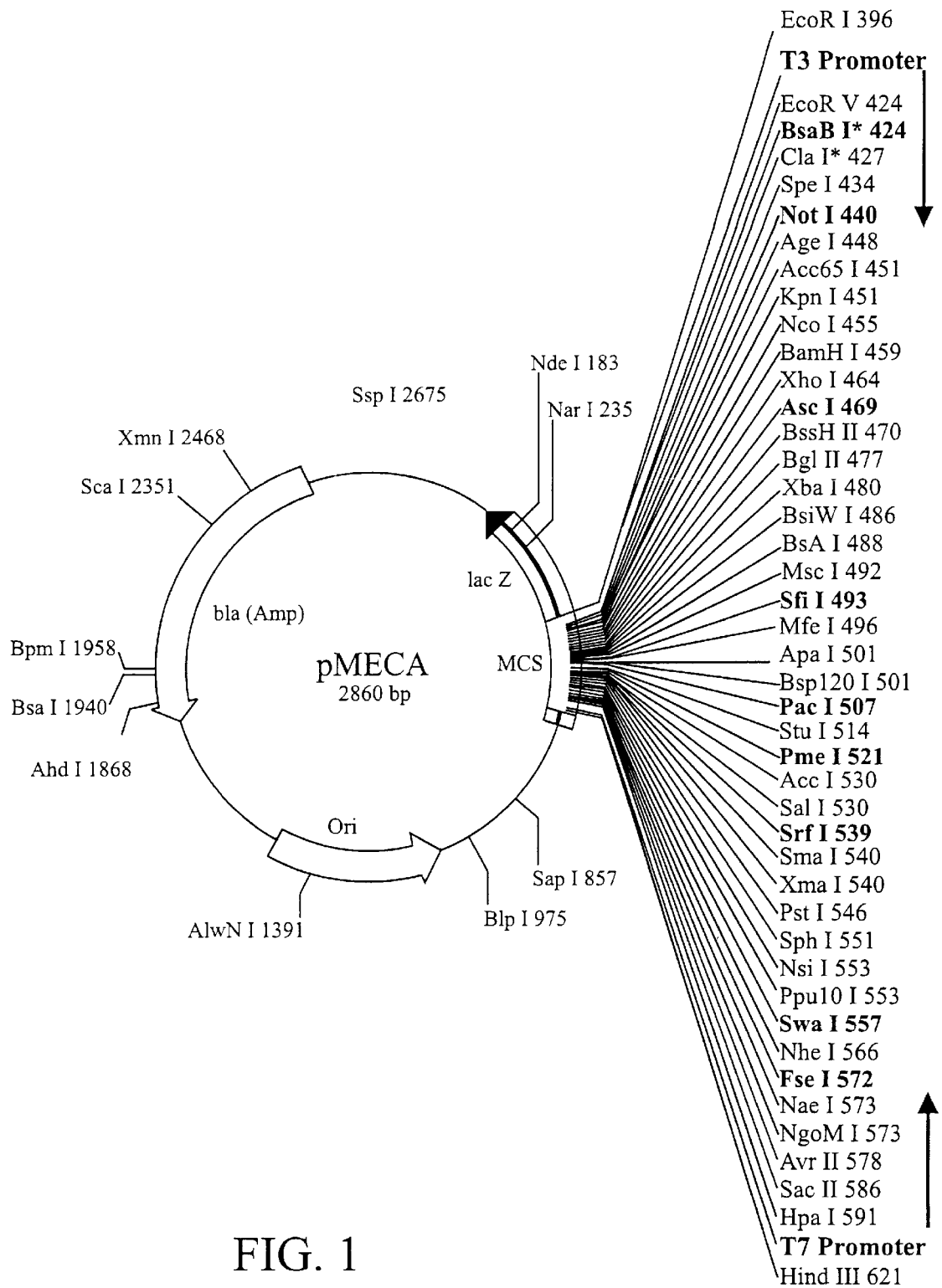
FIG. 1 is a diagram and physical map of pMECA. The multiple cloning site (MCS) has been expanded to the right to show the restriction sites and their order within the MCS. Also shown are the T3 and T7 promoters flanking the MCS together with their direction of transcription, marker genes lac Z and ampicillin resistence (Amp) and origin of replication (Ori). Also shown are various restriction site markers within the vector, outside the MCS.

FIG. 1 diagrams the salient features of pMECA. The vector is based on pUC19 with a multiple cloning site having 44 unique restriction sites fused to a lac Z gene. The multiple cloning site is flanked by T3 and T7 bacteriophage promoters. Positive transformants can be detected either by disruption of the lac Z gene for blue/white screening or by a change in colony size from small to large, a unique characteristic of the pMECA vector. The sequence of the pMECA polylinker is given in Table 1 and also in SEQ ID NO:1.

Figure 2:
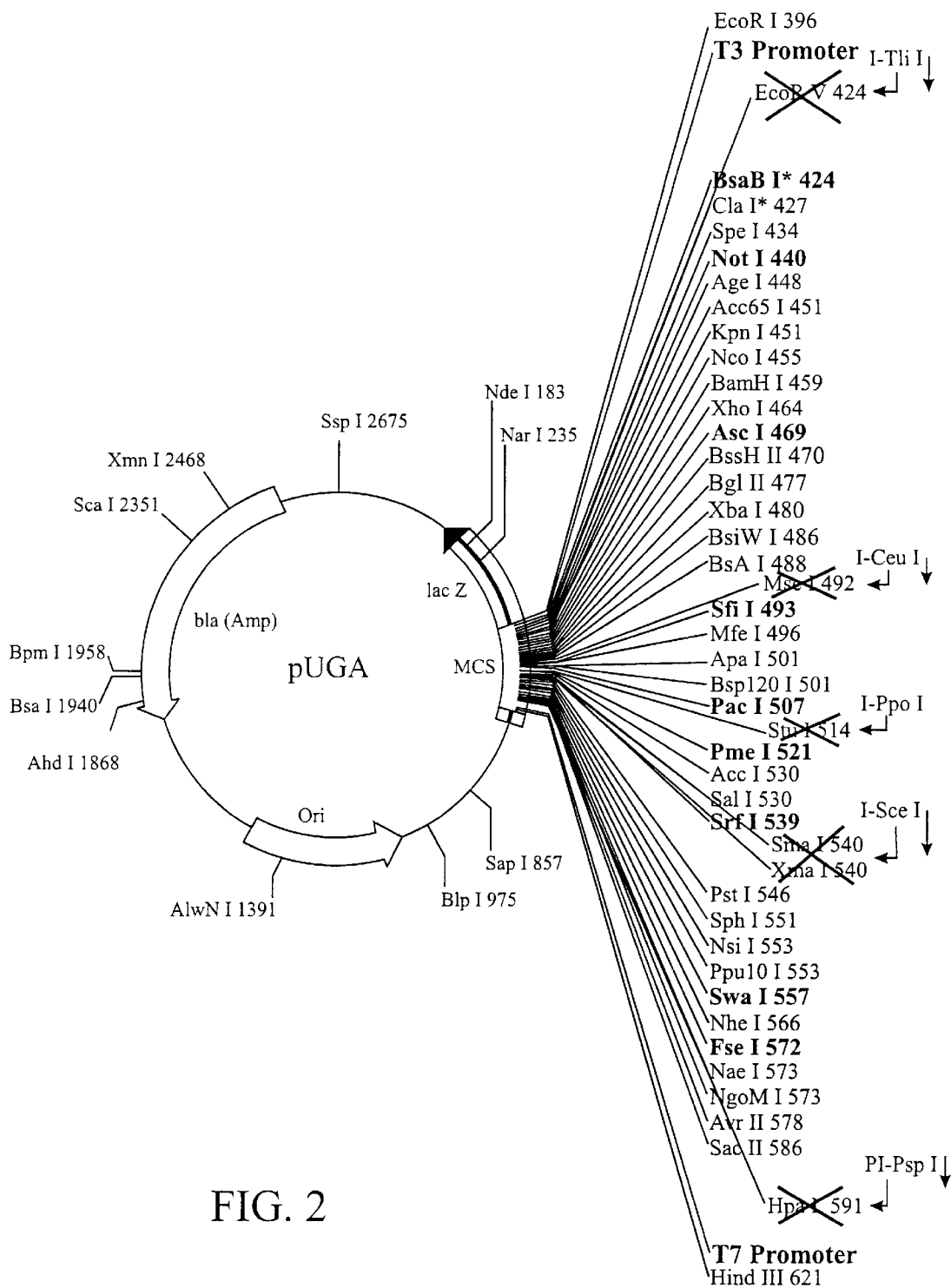
FIG. 2 is a diagram and physical map of pUGA. Location of rare-cutting endonuclease sites are shown beside the sites in pMECA which were removed by insertion of the rare-cutter sites. Downward-pointing arrows beside each rare-cutter site indicate insertion in "forward" order, except for I-Ppo which lacks polarity.

FIG. 2 is a diagram of pUGA, a docking vector having the five rare-cutting endonuclease sites introduced into the pMECA multiple cloning site: I-TliI, I-CeuI, I-PpoI, PI-Sce-I, PI-PspI. In principle, any rare cutting endonuclease site can be employed in constructing such a vector. The five were chosen for convenience, since the respective endonucleases are currently commercially available. The order of placement of the restriction site sequence segments (linkers) is not critical and was selected for convenience of construction. In FIG. 2 the rare-cutting endonuclease sites are shown in "forward" orientation. In Table 2, the sequences of the linkers used to insert each rare-cutting site into the vector is shown as well as the respective cleavage sites, in "forward" orientation. The sequences are also shown as follows: SEQ ID NO:2: I-CeuI linker; SEQ ID NO:3: I-PpoI; SEQ ID NO:4: PI-PspI linker; SEQ ID NO:5; PI-SceI linker; SEQ ID NO:6: I-TliI linker. Other rare-cutting restriction endonucleases are known. Reference is made, e.g. to Lambowitz, A. M., et al. (1993) supra, for examples of other known rare-cutters suitable for use in the present invention. The analysis of any vector or DNA segment for existence of a rare-cutter site (or any restriction site), can be carried out experimentally, by analyzing gel electrophoretic mobility before and after incubation of the DNA with the appropriate enzyme, or by sequence analysis, using any of several sequence analysis programs known in the art, provided the sequence is known.

In FIG. 3 one example of a shuttle vector is diagramed. In general, a shuttle vector will have at least two rare cutter restriction sites in congruent orientation with at least one other restriction site between them. Shuttle vectors based on pMECA are further designated according to the rare-cutter sites they possess and the orientation of the sites. The specificity of each site is designated but the orientation is only designated once. For example, pMECA/I-CeuI-I-CeuI/For has two I-CeuI sites in forward orientation. Its counterpart, pMECA/I-CeuI-I-CeuI/Rev, having the two I-CeuI sites in reverse orientation is also shown. The vector pMECA/I-TliI-I-CeuI/For has an I-TliI site and an I-CeuI site in forward orientation. A shuttle vector such as pMECA/I-CeuI-I-CeuI/For is then used as follows: The DNA segment of interest is inserted into pMECA/I-CeuI-I-CeuI/For by a conventional insertion process, using any of the conventional restriction sites of the multiple cloning site as may be convenient, depending on the type of sites convenient for the particular DNA segment, as is known in the art. After ligation, the shuttle vector having the DNA segment inserted, is now re-cut using the I-CeuI endonuclease. The DNA segment is excised from the shuttle and carries I-CeuI-specific ends and can then be inserted into the I-CeuI/For site of a docking vector such as pUGA. By using five such shuttle vectors bearing pairs of rare-cutter sites, in a sequence of step up to five DNA segments can be combined into the same docking vector.

Shuttle vectors having two different rare-cutter sites can also be used. Preferably, the two sites chosen would be those lying adjacent on the docking vector. For example, using pUGA as a docking vector, a shuttle having I-CeuI site and a I-TliI site can be constructed. A gene or other DNA segment of choice can be inserted into a conventional site between the two rare-cutter sites and then removed from the vector by a combination of I-CeuI and I-TliI endonucleases. The excised DNA can then be inserted in pUGA cut by the same two enzymes. The insertion then generates the I-CeuI and I-TliI sites on pUGA, with the DNA segment of choice inserted between them. By using selected pairs of restriction sites with their associated shuttles, in the manner just described, up to four separate DNA segments can be sequentially combined into pUGA. Furthermore, the original restriction sites are reconstituted, after insertion, allowing for up to five additional single-site insertions, as described previously, at each of the five sites. A total of up to nine insertions can be sequentially combined by the described methods. Since a given insertion can have more than one gene, nine segments could have more than nine genes.

In accord with the foregoing description, a specific example of the invention is herein described in detail: construction of pMECA, construction of pUGA and use of shuttle vectors to assemble into the pUGA docking vector a set of DNA segments from different sources into a single cluster, termed a gene artificial cluster (GAC) herein. All terms and abbreviations used are standard or commonly used in the art and in journals and texts commonly consulted by those skilled in the art. Basic techniques are generally described in Sambrook et al., *Molecular Cloning—A Laboratory Manual*, Cold Spring Harbor Laboratory, New York (1989) in the multi-volume *Methods in Enzymology*, Academic Press, New York, as well as in other well-known texts and manuals.

EXAMPLE 1

Construction of pMECA
Materials and Methods

A 230-bp synthetic polylinker was designed by computer analysis using the software packages MacDNAsis 2.0 (Hitachi Software Engineering America, Ltd., San Bruno, Calif.) and Oligo 4.0 (National Biosciences, Inc., Plymouth. Minn.) as a lacZ gene fusion into the EcoRI/HindIII sites of pUC19. Six oligonucleotides of 57 to 59 bases containing 23-nucleotide overlaps were synthesized (Operon Technologies, Inc., Alameda, Calif.) and used in a two-step overlap extension-PCR as defined by Dillon and Rosen (1990) *Biotechniques* 9:298–300 with a Roboclycler 9600 Gradient Thermocycler (Stratagene, La Jolla, Calif.). The reaction mixture consisted of 10 mM KCl, 10 mM $(NH_4)_2SO_4$, 20 mM Tris-HCl (pH 8.75), 2 mM $MgSO_4$, 0.1% Triton® X-100, 100 µg/ml BSA, 200 µM dNTPs, 400 µM each oligonucleotide and 2.5 units cloned Pfu DNA Polymerase (Stratagene, La Jolla, Calif.) in a 50 µl volume. Thermocycling conditions were as follows: initial denaturation of 94° C. for 5 min. and seven cycles of (94° C. for 1.5 min, 75 ° C. for 3 min). One µl of the PCR reaction was used for the second round of amplification with flanking oligonucleotides. Reaction conditions were as previous stated, except 200 µM each oligonucleotide were substituted for oligonucleotides. Thermocycling conditions were as follows: initial denaturation of 94° C. for 5 min. and 20 cycles of (94° C. for 1 min, 60° C. for 1 min, and 72° C. for 1 min) with a final extension of 72° C. for 7 min. The PCR product was digested with EcoRI and HindIII and purified by agarose gel electrophoresis, Heyd, M. L. et al. (1996) *Biotechniques* 29:394–398. The purified DNA fragment was ligated into the EcoRI/HindIII sites of pUC19, to create pMECA, for Multiple Enzymatic Cloning Area. The nucleotide sequence of the pMECA polylinker is shown in Table 1 (SEQ ID NO:1).

Colonies containing the insert were confirmed by PCR using the T3 and T7 bacteriophage promoter primers which are absent in pUC 19. Bacteria were transferred from agar plates by sterile pipette tips to a PCR tube containing 30 µl reaction mix as follows; 50 mM KCl, 10 mM Tris-HCl, pH 9.0, 0.1% Triton X-100® 2.0 mM $MgCl_2$, 200 mM each T3 and T7 primers, 200 µM each dNTP, and 1.5 U Taq DNA polymerase (Promega, Madison, Wis.).

Thermocycling conditions were as follows: initial denaturation of 94° C. for 5 min and 30 cycles of (94° C. for 0.5 min, 60° C. for 0.5 min, and 72° C. for 0.5 min) with a final extension of 72° C. for 5 min. Positive clones were confirmed by agarose gel electrophoresis and sequencing. To test cloning efficiency, the plasmid pBSL86 (Alexander, M. F. [1995] *Biotechniques* 18:52–56) was digested with either PstI or double digested with KpnI/NheI and the fragment containing the neomycinphosphotransferase II gene (nptII) resistance cassette was gel-purified as before. The fragments were ligated into either PstI or double digested KpnI/NheI pMECA and transformed into DH5α. Bacteria were selected on LB agar plates supplemented with 100 μg/ml ampicillin alone or with 0.1 mM IPTG and 20 μg/ml Xgal. Seven hundred small and 700 large colonies were selected from the ampicillin plates and an additional 700 blue and 700 white colonies were selected from the ampicillin plates supplemented with IPTG/Xgal. All selected colonies were transferred to grid plates containing LB agar supplemented with 30 μg/ml kanamycin and scored for growth after 16 hours of incubation at 37° C.

Nucleotide sequence analysis revealed the existence of all 44 restriction sites with no mutations. We have named this new vector pMECA (for Multiple Enzymatic Cloning Area) (FIG. 1). Bacterial clones that are transformed by this plasmid vector are light blue in color as compared to those transformed by the parental pUC19 plasmid (data not shown). The reason for this reduction in β-galactosidase activity is unclear, however an analysis of the polylinker for codon usage and RNA folding patterns has revealed a large hairpin. Furthermore, bacterial colonies are significantly larger when the polylinker is disrupted by cloning a DNA fragment into it, even one as small as 23 bp. We have used this distinct morphological change in bacterial colony size, instead of β-galactosidase activity, as an indicator of positive transformants with a success rate of nearly 100%. The observed reduction in bacterial replication or colony size has not affected plasmid yields. While this vector can be used for blue/white screening by conventional techniques, colonies containing an insert can be identified just as effectively by simply selecting the larger colonies thus eliminating the need for IPTG and Xgal. Complete nucleotide sequence of pMECA is available from Genbank as accession #AF017063.

EXAMPLE 2

Construction of pUGA and Shuttle Vectors
Materials and Methods

Linkers were synthesized and PAGE- and reverse HPLC-purified by New England Biolabs (Table 2). A reaction to add non-templated dATP to the 3'-OH ends of the linkers used 1 pM of each linker incubated with 200 μM dATP and 2.5 U Taq DNA Polymerase at 72° C. for 3 hours. Linkers were ligated into either HpaI, EcoRV, MscI, SmaI, or StuI-digested pMECA (Thomson and Parrott, [1998] *BioTechniques* 24:922–927, incorporated herein by reference) which had the non-templated addition of dTTP to the 3'-OH ends as described above. Ligated plasmids were transformed into DH5α and plated on Luria-Bertani agar plates containing 100 μg/mL ampicillin. Initial recombinants were determined by large colony screening (Thomson and Parrott, 1998) and subsequently confirmed by PCR. Initially, PCR was performed using the T3 and T7 promoter primers, followed by combinations of T3 or T7 with the various linker-specific primers. Once single integrations were confirmed by PCR and sequencing, the vectors were digested with various restriction enzymes and shuffled together to generate both pUGA and the shuttles (FIG. 3). An Agrobacterium-based vector, pPZP203, was generated by digesting pUGA with EcoRI and HindIII to liberate the multiple cloning site, which was subsequently cloned into the corresponding sites of pPZP201 (Hajdukiewicz P. et al., [1994] *Plant Mol. Biol.* 25:989–994). The sites of linker integration within the various vectors are in Table 3.

All restriction enzymes and linkers were from New England Biolabs, Taq DNA Polymerase was from Promega, dNTPs were from Amresco, primers were from Operon Technologies, and all other chemicals were from Fisher. DNA fragments were purified from gels as described by Thomson and Compton (1998) *BioTechniques* 24:942. Conditions for the enzymatic manipulation of the homing endonucleases are similar to those for standard bacterial type II enzymes. Ligation of the homing endonuclease sites are also as those for the standard bacterial type II cleavage sites. The exception was that PI-PspI required an overnight digestion to give complete cutting. Details on digestion with these homing endonucleases is in Table 4.

EXAMPLE 3

Gene Stacking using the Vector System

A simple process for sequentially combining two specified DNA gene segments is described using pUGA as docking vector, and two shuttle vectors, pMECA/I-TliI-I-TliI/For as first shuttle vector, and pMECA/I-CeuI-I-CeuI/For as second shuttle vector. A first specified DNA segment is provided with (or is known to possess) flanking restriction site sequences for a conventional restriction site ofthe pMECA multiple cloning site, for example, ClaI. The first shuttle vector is cut with ClaI endonuclease and the first specified DNA segment is inserted therein by a DNA-ligase-catalyzed reaction, under conditions known in the art. The first specified DNA segment is then excised from the shuttle vector by the action of I-CeuI endonuclease.

The first specified DNA excised from the shuttle vector by I-CeuI endonuclease now has overlapping single stranded ends specific to I-CeuI and is inserted into pUGA, previously cut with I-CeuI endonuclease, in a DNA ligase-catalyzed reaction.

In similar fashion, the second specified DNA segment is first inserted into the second shuttle vector, excised by the I-TliI endonuclease, and inserted into I-TliI-cut pUGA (conveying the first specified DNA) using DNA ligase. In this manner, the first and second specified DNA segments are sequentially combined into the docking vector pUGA. Additional DNA segments can be sequentially combined, as described. The orientation of the DNA segments is determined by their orientation in the shuttle vector. The order of the DNA segments as combined in the docking vector is determined by the order of the rare-cutting restriction sites in the docking vector. For example, as described above, the second DNA segment lies closer to the lacZ gene than does the first segment, since the I-TliI site on pUGA lies closer to lacZ than does the I-CeuI site.

It will be appreciated by those skilled in the art that the order and orientation of DNA segments sequentially combined in the docking vector can be controlled by the choice of shuttle vectors and orientation thereof, as described.

TABLE 1

```
           400              420                440
              T3 Promoter-->  +1
          •                •  #      ClaI*      • NotI
    AGTGAATTCACATTAACCCTCACTAAAGGGAGATATCGATCACTAGTGCGGCCGCACCGG
       EcoRI                     EcoRV      SpeI         AgeI
                                 BSaBI*

460              480                500
                                  BsiWI
       NcoI •    XhoI BssHII Bgl•II    SplI    SfiI •
    TACCATGGATCCTCGAGGCGCGCCAGATCTAGACGTACGTGGCCAATTGGGCCCTTAATT
      KpnI    BamHI    AscI     XbaI   BsaAI    MfeI         PacI
    Acc65I                                 MscI     ApaI
                                                    Bsp120I 520              540                560
                              •SrfI         SphI•
          •
    AAGGCCTCGTTTAAACAGTCGACGTCGCCCGGGCTGCAGCATGCATTTAAATGGCTAGCG
       StuI    PmeI    SalI     SmaI  PstI  NsiI         NheI
                       AccI     XmaI              SwaI 580              600                620
    NaeI
      NgoMI •         HpaI     •         •HindIII
    GCCGGCCTAGGGACCGCGGTTAACATCTCCCTATAGTGAGTCGTATTAAAGCTTGGCGTA
      FseI       SacII           #
         AvrII                  +1 <-- T7 Promoter 640
          •
    ATCATGGTCAT
              1
    MetThrMet <--LacZ
```

TABLE 2

Linkers used in construction of pUGA.
Gaps indicate cleavage sites.

```
• I-Ceu I    5'-TAACTATAACGGTCCTAA ▼    GGTAGCGA-3'
  26 mer     3'-ATTGATATTGCCAG     GATTCCATCGCT-5'

• I-Ppo I    5'-ATGACTCTCTTAA     GGTAGCCAAA-3'
  23 mer     3'-TACTGAGAG      AATTCCATCGGTTT-5'

• PI-Psp I   5'-TGGCAAACAGCTATTAT    GGGTATTATGGGT-3'
  30 mer     3'-ACCGTTTGTCGAT    AATACCCATAATACCCA-5'

• PI-Sce I   5'-ATCTATGTCGGGTGC    GGAGAAAGAGGTAATGAAATGGCA-3'
  39 mer     3'-TAGATACAGCC    CACGCCTCTTTCTCCATTACTTTACCGT-5'

• I-Tli I    5'-GGTTCTTTATGCGGACAC    TGACGGCTTTATG-3'
  31 mer     3'-CCAAGAAATACGCC    TGTGACTGCCGAAATAC-5'
```

TABLE 3

Sites of linker integration within pUGA and the various shuttle vectors.

| Vector | Linker | Site |
|---|---|---|
| pUGA | I-TliI | EcoRV |
| | I-CeuI | MscI |
| | I-PpoI | StuI |
| | PI-SceI | SmaI |
| | PI-PspI | HpaI |
| pPZP203 | I-TliI | EcoRV |
| | I-CeuI | MscI |
| | I-PpoI | StuI |
| | PI-SceI | SmaI |
| | PI-PspI | HpaI |
| pMECA/I-PpoI-I-PpoI | I-PpoI | EcoRV |
| | I-PpoI | HpaI |
| pMECA/PI-PspI-PI-PspI/For | PI-PspI | EcoRV |
| | PI-PspI | HpaI |
| pMECA/I-CeuI-I-CeuI/For | I-CeuI | EcoRV |
| | I-CeuI | HpaI |
| pMECA/I-CeuI-I-CeuI/Rev | I-CeuI | EcoRV |
| | I-CeuI | HpaI |
| pMECA/PI-SceI-PI-SceI/For | PI-SceI | EcoRV |
| | PI-SceI | HpaI |
| pMECA/I-TliI-I-TliI/For | I-TliI | EcoRV |
| | I-TliI | HpaI |
| pMECA/I-PpoI-PI-SceI(For) | I-PpoI | EcoRV |
| | PI-SceI | HpaI |
| pMECA/PI-SceI-PI-PspI/For | PI-SceI | EcoRV |
| | PI-PspI | HpaI |
| pMECA/I-TliI-PI-PspI/For | I-TliI | EcoRV |
| | PI-PspI | HpaI |
| pMECA/I-TliI-I-CeuI/For | I-TliI | EcoRV |
| | I-CeuI | HpaI |
| pMECA/I-CeuI(For)-I-PpoI | I-CeuI | I-PpoI |
| | EcoRV | HpaI |

TABLE 4

Manufacturer's recommendations for the homing endonucleases used in this study. Note the deviation from these specifications, as described in the Materials and Methods for PI-PspI.

| Enzyme | Units | Amount of DNA Cut | Time Required | Temperature | Reaction Volume |
|---|---|---|---|---|---|
| I-CeuI | 0.5 | 1 µg | 3 hours | 37° C. | 50 µl |
| I-PpoI | 0.1 | 1 µg | 1 hour | 37° C. | 50 µl |
| PI-PspI | 0.5 | 1 µg | 1 hour | 65° C. | 50 µl |
| PI-SceI | 1.0 | 1 µg | 3 hour | 37° C. | 50 µl |
| I-TliI | 1.0 | 1 µg | 1 hour | 50° C. | 50 µl |

What is claimed is:

1. A set of vectors for sequentially combining a plurality of specified DNA segments in a desired order and a desired orientation comprising a docking vector and a set of shuttle vectors, the docking vector having a multiple cloning site having a plurality of rare-cutting restriction endonuclease sites, each of said sites being present at a single locus in the vector, each shuttle vector comprising at least two rare-cutting endonuclease sites corresponding to one or more rare-cutting endonuclease sites of the docking vector in congruent orientation with one another and further comprising at least one other restriction site between the rare-cutting restriction sites.

2. The set of vectors of claim 1 wherein the rare-cutting endonuclease sites are selected from the group consisting of I-TliI, I-CeuI, I-PpoI, PI-SceI and PI-PspI.

3. The set of vectors of claim 1 wherein the set of shuttle vectors comprises a separate shuttle vector for each rare-cutting site on the docking vector.

4. The set of vectors of claim 3 further comprising a pair of shuttle vectors for each rare-cutting site on the docking vector except I-PpoI, each member of the pair of shuttles having its rare-cutter sites in either forward or reverse orientation.

5. The set of vectors of claim 3 wherein the set of shuttle vectors comprises a separate shuttle vector for each of two rare-cutter sites located nearest one another on the docking vector.

6. The set of vectors of claim 4 wherein the docking vector is pUGA and the set of shuttle vector comprises pMECA/I-TliI-I-TliI/For, pMECA/I-CeuI-I-CeuI/For, pMECA/I-PpoI-I-PpoI, pMECA/PI-SceI-PI-SceI/For and pMECA/PI-PspI-PI-PspI/For.

7. The set of vectors of claim 5 wherein the docking vector is pUGA and the set of shuttle vectors comprises pMECA/I-Tli-I-CeuI/For, pMECA/I-CeuI(For)-I-PpoI, pMECA/I-PpoI-PI-SceI-(For), and pMECA/PI-SceI-PI-PspI/For.

8. A kit for sequentially combining a plurality of specified DNA segments in a desired order and a desired orientation comprising a set of vectors according to claim 1 and samples of purified rare-cutting restriction endonuclease specific for each rare-cutter site of the docking vector.

9. A kit for sequentially combining a plurality of specified DNA segments in a desired order and a desired orientation comprising a set of vectors according to claim 6 and samples of purified rare-cutting endonuclease specific for each of I-TliI, I-CeuI, I-PpoI, PI-SceI and PI-PspI.

10. A kit according to claim 9 further comprising the set of shuttle vectors pMECA/I-Tli-I-CeuI/For, pMECA/I-CeuI (For)-I-PpoI, pMECA/I-PpoI-PI-SceI-(For), and pMECA/PI-SceI-PI-PspI/For.

11. A shuttle vector comprising at least two rare-cutter restriction sites in congruent orientation and further comprising at least one other restriction site between the rare-cutter restriction sites.

12. A shuttle vector according to claim 11 wherein the two rare-cutter restriction sites are different from one another.

13. The shuttle vector of claim 11 wherein the rare-cutter restriction sites are selected to be one of the pairs I-TliI and I-TliI, I-CeuI and I-CeuI, I-PpoI and I-PpoI, PI-SceI and PI-SceI, PI-PspI and PI-PspI, I-TliI and I-CeuI, I-CeuI and I-PpoI, I-PpoI and PI-SceI, and PI-SceI and PI-PspI.

14. The shuttle vector of claim 11 selected from the group pMECA/I-TliI-I-TliI/For, pMECA/I-TliI-I-TliI/Rev, pMECA/I-CeuI-I-CeuI/For, pMECA/I-CeuI-I-CeuI/Rev, pMECA/I-PpoI-I-PpoI, pMECA/PI-SceI-PI-Sce I/For, pMECA/PI-SceI-PI-SceI/Rev, pMECA/PI-PspI-PI-PspI/For, pMECA/PI-PspI-PI-PspI/Rev, pMECA/I-TliI-I-CeuI/For, pMECA/I-CeuI(For)-I-PpoI, pMECA/I-PpoI-PI-SceI (For), or pMECA/PI-SceI-PI-PspI/For.

15. A method for sequentially combining a plurality of specified DNA segments in a desired order and a desired orientation into a vector comprising:

a) providing a docking vector having a multiple cloning site comprising a plurality of rare-cutting restriction endonuclease sites, each of said sites being present at a single locus in the docking vector, b) further providing a plurality of shuttle vectors comprising at least two rare-cutting endonuclease sites in congruent orientation with one another and further comprising at least one other restriction site between the rare-cutting restriction sites, c) inserting a first specified DNA segment into a first shuttle vector, d) excising the first specified DNA segment from the shuttle vector by the action of a rare-cutting endonuclease specific for a rare-cutting restriction site on said vector, thereby providing said first specified DNA excised with ends specific for said endonuclease, e) inserting the excised first specified DNA into the docking vector at a rare-cutting restriction site corresponding to the site on the first shuttle vector, and f) repeating steps (c), (d), and (e) using another specified DNA and another shuttle vector, whereby a plurality of specified DNA segments is combined into the docking vector in desired order and desired orientation.

16. The method of claim 15 wherein the docking vector is pUGA.

17. The method of claim 15 wherein the shuttle vectors comprise pMECA/I-TliI-I-TliI/For, pMECA/I-TliI-I-TliI/Rev, pMECA/I-CeuI-I-CeuI/For, pMECA/I-PpoI-I-PpoI, pMECA/PI-SceI-PI-SceI/For,pMECA/PI-SceI-PI-SceI/Rev, pMECA/PI-PspI-PI-PspI/For, pMECA/PI-PspI-PI-PspI/Rev, pMECA/I-TliI-I-CeuI/For, pMECA/I-CeuI(For)-I-PpoI, pMECA/I-PpoI-PI-SceI(For), or pMECA/PI-SceI-PI-PspI/For.

18. A multiple cloning site vector having a multiple cloning site containing restriction site sequences specific for the restriction endonucleases EcoRV, BsaBI, ClaI, SpeI, NotI, AgeI, Acc65I, KpnI, NcoI, BamHI, XhoI, AscI, BssHII, BglII, XbaI, BsiWI, BsaAI, MscI, SfiI, MfeI, ApaI, Bsp120I, PacI, StuI, PmeI, AccI, SalI, SrfI, SmaI, XmaI, PstI, SphI, NsiI, Ppu10I, SwaI, NheI, FseI, NaeI, NgoMI, AvrII, SacII, and HpaI.

19. The vector of claim 18 wherein the multiple cloning site has the necleotide sequence of SEQ ID NO:1.

20. The vector of claim 18, wherein the vector is pMECA.

* * * * *